(12) United States Patent
Watanabe

(10) Patent No.: US 10,667,669 B2
(45) Date of Patent: Jun. 2, 2020

(54) ENDOSCOPE SYSTEM HAVING VARIOUS COMBINATIONS OF LIGHT SOURCES

(71) Applicant: HOYA CORPORATION, Tokyo (JP)

(72) Inventor: Hiroyuki Watanabe, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 437 days.

(21) Appl. No.: 15/511,081

(22) PCT Filed: Aug. 2, 2016

(86) PCT No.: PCT/JP2016/072628
§ 371 (c)(1),
(2) Date: Mar. 14, 2017

(87) PCT Pub. No.: WO2017/026323
PCT Pub. Date: Feb. 16, 2017

(65) Prior Publication Data
US 2017/0273541 A1 Sep. 28, 2017

(30) Foreign Application Priority Data
Aug. 12, 2015 (JP) ................. 2015-159403

(51) Int. Cl.
*A61B 1/06* (2006.01)
*A61B 1/04* (2006.01)
(Continued)

(52) U.S. Cl.
CPC ........ *A61B 1/00004* (2013.01); *A61B 1/0002* (2013.01); *A61B 1/00022* (2013.01);
(Continued)

(58) Field of Classification Search
CPC ............ A61B 1/00004; A61B 1/00006; A61B 1/0002; A61B 1/00022; A61B 1/00039;
(Continued)

(56) References Cited

U.S. PATENT DOCUMENTS 5,583,566 A * 12/1996 Kanno ................. G11B 27/105
348/72
5,697,885 A * 12/1997 Konomura ........... H04N 1/2175
348/65

(Continued)

FOREIGN PATENT DOCUMENTS

| CN | 101147667 A | 3/2008 |
| CN | 103889307 | 6/2014 |

(Continued)

OTHER PUBLICATIONS

Translation of JP 2012183240, dated Sep. 2012.*

(Continued)

*Primary Examiner* — John P Leubecker
(74) *Attorney, Agent, or Firm* — Greenblum & Bernstein, P.L.C.

(57) ABSTRACT

An endoscope system includes a video processor device that performs signal processing on an image, and an external device that is removably connected to the video processor device and can record light source correspondence information that corresponds to multiple light sources. The video processor device acquires light source correspondence information from the external device and performs signal processing that corresponds to the light source correspondence information.

6 Claims, 9 Drawing Sheets

(51) Int. Cl.
  *A61B 1/00* (2006.01)
  *G02B 23/24* (2006.01)
  *G02B 23/26* (2006.01)

(52) U.S. Cl.
  CPC ............ *A61B 1/00039* (2013.01); *A61B 1/04* (2013.01); *A61B 1/0638* (2013.01); *A61B 1/0669* (2013.01); *G02B 23/2484* (2013.01); *A61B 1/00006* (2013.01); *A61B 1/00059* (2013.01); *G02B 23/2461* (2013.01); *G02B 23/26* (2013.01)

(58) Field of Classification Search
  CPC ............ A61B 1/00059; A61B 1/00057; A61B 1/0661; A61B 1/0669
  See application file for complete search history.

(56) References Cited

U.S. PATENT DOCUMENTS

| | | | |
|---|---|---|---|
| 6,436,032 B1* | 8/2002 | Eto ................... | A61B 1/00059 600/117 |
| 6,943,822 B2* | 9/2005 | Iida ..................... | H04N 1/6086 348/65 |
| 8,581,972 B2 | 11/2013 | Iwasaki | |
| 2001/0002842 A1* | 6/2001 | Ozawa ............... | A61B 1/00039 348/45 |
| 2004/0044269 A1* | 3/2004 | Shibata ............... | A61B 5/0002 600/101 |
| 2007/0049798 A1* | 3/2007 | Urasaki ............. | A61B 1/00011 600/118 |
| 2007/0100202 A1* | 5/2007 | Murata .............. | A61B 1/00059 600/109 |
| 2007/0123749 A1* | 5/2007 | Iwasaki ............. | A61B 1/00055 600/117 |
| 2008/0074492 A1* | 3/2008 | Iwasaki ............. | A61B 1/00059 348/68 |
| 2008/0143827 A1* | 6/2008 | Yoshizumi ......... | A61B 1/00059 348/65 |
| 2009/0027490 A1 | 1/2009 | Hirai et al. | |
| 2016/0088999 A1* | 3/2016 | Langell ............. | A61B 1/00006 348/68 |
| 2017/0071678 A1* | 3/2017 | Uchida .............. | A61B 1/00006 |
| 2017/0100018 A1* | 4/2017 | Saito ........................ | A61B 1/00 |
| 2017/0231471 A1* | 8/2017 | Nishio .................... | A61B 1/06 348/67 |
| 2017/0325670 A1* | 11/2017 | Koizumi ........... | A61B 1/00006 |
| 2017/0332889 A1* | 11/2017 | Akiba ..................... | A61B 1/05 |
| 2018/0042454 A1* | 2/2018 | Iwasaki ............. | A61B 1/00009 |

FOREIGN PATENT DOCUMENTS

| | | | | |
|---|---|---|---|---|
| JP | 11-9547 | | 1/1999 | |
| JP | 2001-70240 | | 3/2001 | |
| JP | 2006-334323 | | 12/2006 | |
| JP | 2008-23017 | | 2/2008 | |
| JP | 2011-110104 | | 6/2011 | |
| JP | 2012183240 A | * | 9/2012 | ........ A61B 1/00009 |
| WO | 2015/194422 | | 12/2015 | |

OTHER PUBLICATIONS

Search Report and Written Opinion issued in WIPO Patent Application No. PCT/JP2016/072628, dated Sep. 6, 2016.

Office Action issued in Chinese family member Patent Appl. No. 201680002808.0, dated Sep. 4, 2019.

Office Action issued in Japan family member Patent Appl. No. 2015-159403, dated Jan. 7, 2020.

* cited by examiner

ENDOSCOPE SYSTEM HAVING VARIOUS COMBINATIONS OF LIGHT SOURCES

TECHNICAL FIELD

The present invention relates to an endoscope system in which various combinations of light sources and endoscopes can be used.

BACKGROUND ART

In order for appropriate white balance adjustment that corresponds to individual lamps for use to be executed in a simple manner in a video processor for an electronic endoscope equipped with multiple lamps, a configuration has been proposed in which the video processor is provided with a memory that stores white balance adjustment data that corresponds to the lamps (see Patent Document 1).

PRIOR ART DOCUMENT

Patent Document

Patent Document 1: JP 2011-110104A

SUMMARY OF INVENTION

Technical Problem

However, with the configuration in Patent Document 1, video processors used in the same environment each need to be provided with a new memory for storing data for each light source, and it is difficult to apply this configuration to existing systems, for example. Also, in cases of using a light source other than the lamp of the video processor, such as when performing stroboscopic imaging, it is not possible to apply the same configuration and perform white balance adjustment.

An issue addressed by the present invention is enabling central management of information regarding light sources and improving operation efficiency in an endoscope system in which various combinations of multiple types of light sources, video processors, and endoscopes are used.

Solution to Problem

An endoscope system of the present invention includes: a video processor device that performs signal processing on an image; and an external device that is removably connected to the video processor device and can store light source correspondence information that corresponds to a plurality of light sources, wherein the video processor device acquires the light source correspondence information from the external device and performs signal processing that corresponds to the light source correspondence information.

It is preferable that the external device includes an input means for setting a type of examination, and the video processor device acquires, from the external device, light source correspondence information that corresponds to a type of examination that was set. The light source correspondence information includes a white balance parameter, and the signal processing includes white balance adjustment processing. The endoscope system further includes a light source device that is independent of the video processor device, the external device can record light source correspondence information that corresponds to the light source device, and the video processor device can perform signal processing that corresponds to a light source of the light source device. The video processor device may include one or more light sources, and the signal processing is performed based on the light source correspondence information that corresponds to a light source being used. The external device is a filing device, for example. Also, the video processor device can display a message that corresponds to a type of examination that was set.

Advantageous Effects of Invention

According to the present invention, it is possible to perform central management of information regarding light sources and improve operation efficiency in an endoscope system in which various combinations of multiple types of light sources, video processors, and endoscopes are used.

DESCRIPTION OF EMBODIMENTS

Figure 1:
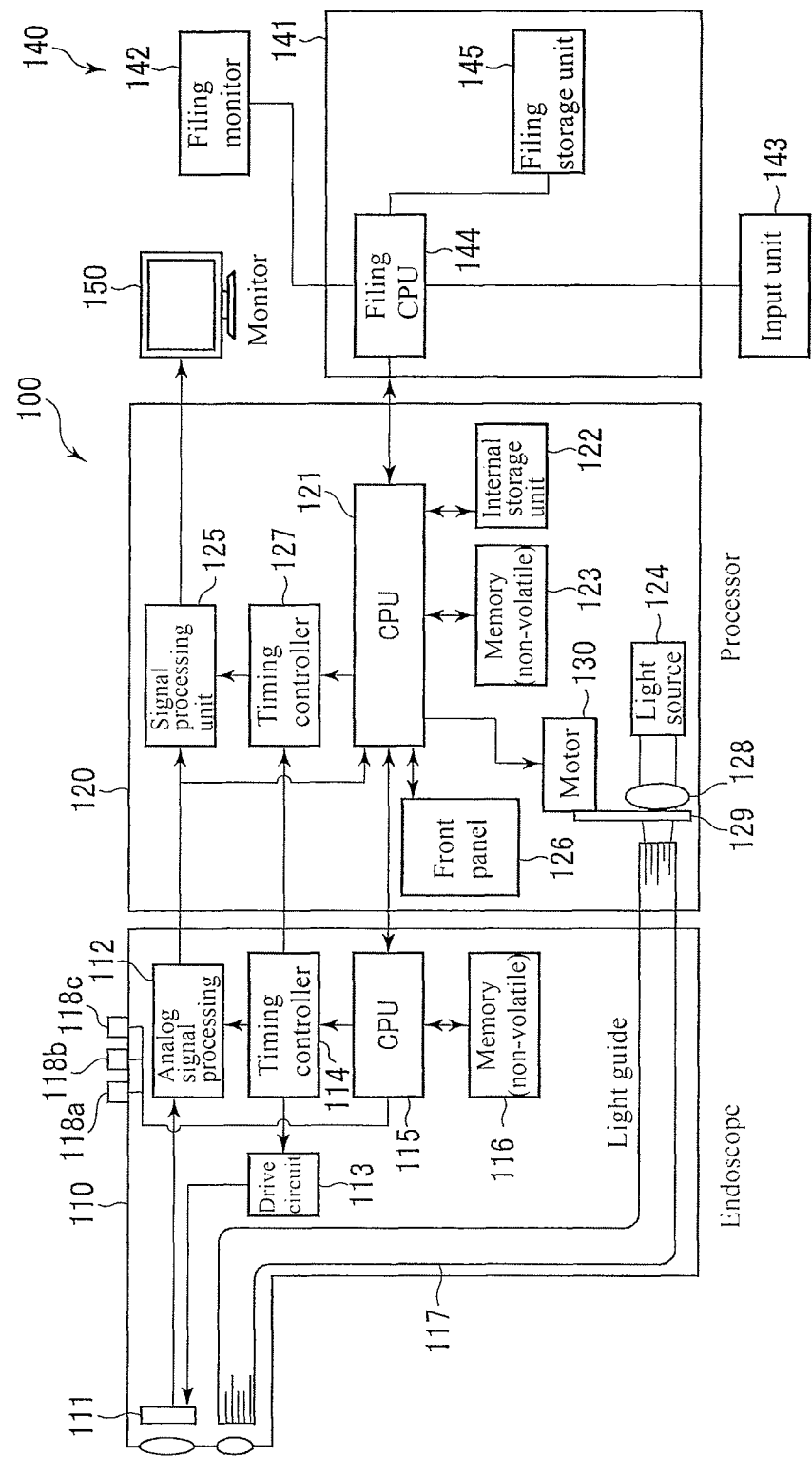
FIG. 1 is a block diagram showing a configuration of an electronic endoscope system that is an embodiment of the present invention in which a processor light source is used for illumination.
Figure 2:
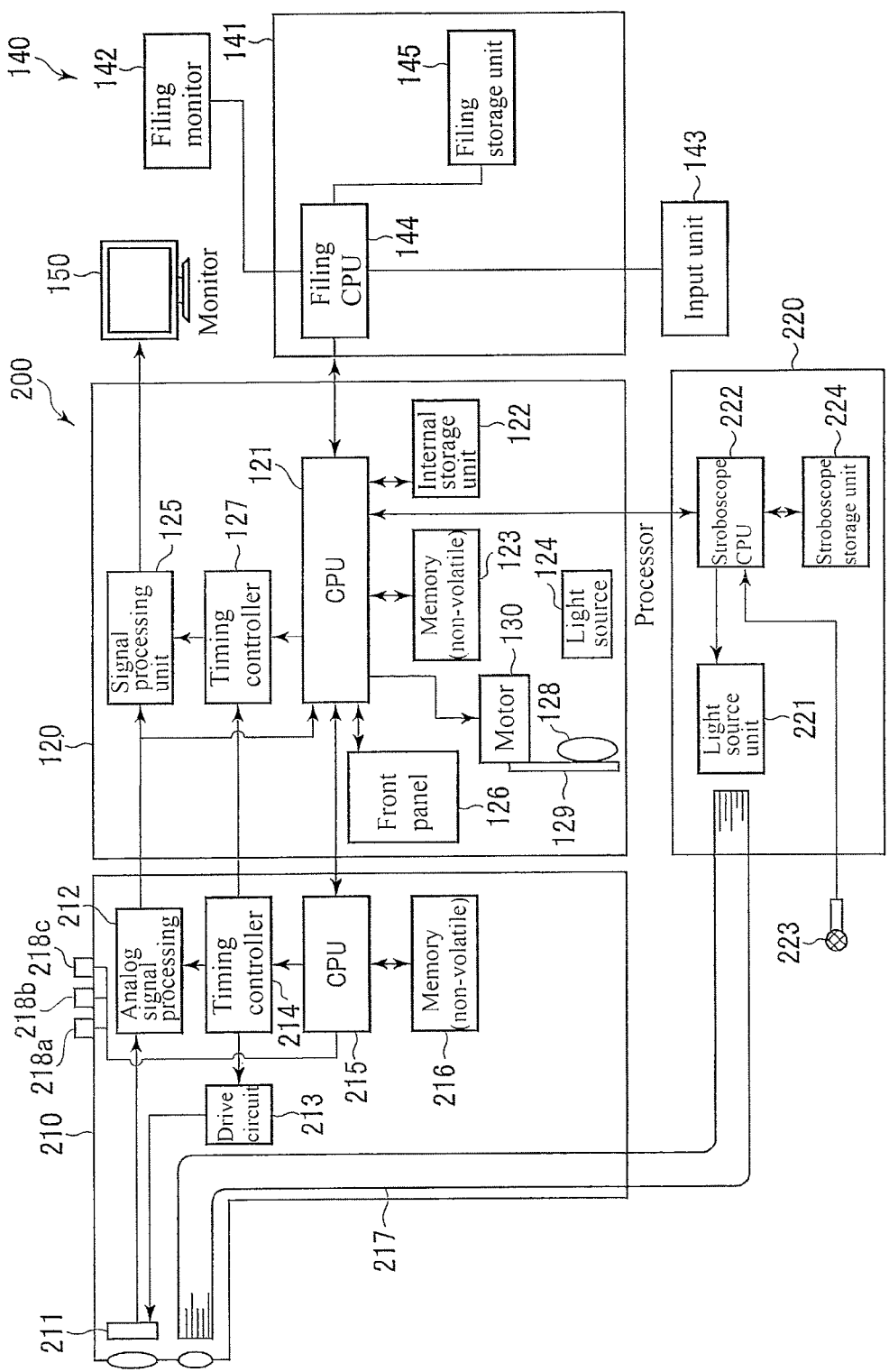
FIG. 2 is a block diagram showing a configuration of an electronic endoscope system that is an embodiment of the present invention in which a stroboscopic light source is used for illumination.

Hereinafter, embodiments of the present invention will be described with reference to the drawings. FIGS. 1 and 2 are block diagrams showing the configurations of endoscope systems that are embodiments of the present invention. Note that FIG. 1 shows a configuration in the case of performing endoscope observation using a light source in the video processor device, and FIG. 2 shows a configuration in the case of performing endoscope observation using a light source other than the light source in the video processor device.

An endoscope system 100 shown in FIG. 1 has a system configuration in the case of using an upper endoscope to observe a stomach, a duodenum, or the like. The endoscope system 100 includes an endoscope 110, a video processor device 120 that is connected to the endoscope 110, a filing device 140 that is removably connected to the video processor device 120 via a network such as a LAN, and a monitor 150 that is connected to the video processor device 120. The endoscope 110 is detachable from the video processor 120, and an appropriate endoscope that corresponds to the type of examination to be carried out and the treatment is attached. An image captured by the endoscope 110 is processed in the video processor device 120, and then displayed on the monitor 150, and also recorded in the filing device 140 along with various additional information as necessary.

The endoscope 110 includes an imaging element 111, an analog signal processing circuit 112, a drive circuit 113, an endoscope timing controller 114, an endoscope CPU 115, an endoscope memory 116, a light guide 117, and endoscope buttons 118a to 118c.

The imaging element 111 is driven by the drive circuit 113. A captured image is converted into a digital signal in the analog signal processing circuit 112 and output to the video processor device 120. The analog signal processing circuit 112 and the drive circuit 113 are subjected to drive timing control by the endoscope timing controller 114, and overall operations of the endoscope 110 are controlled by the endoscope CPU 115. The endoscope CPU 115 is connected to the endoscope memory 116, which stores the device name, the production number, and the like of the endoscope 110, various types of setting information, and the like.

In the endoscope 110 in FIG. 1, the light guide 117 is connected to the video processor device 120. Specifically, light from a light source 124 provided in the video processor device 120 is transmitted as illumination light and emitted from the leading end of the endoscope onto an observation target.

The endoscope buttons 118a to 118c are switches operated by a user (i.e., a doctor), and various functions of the endoscope 110 and the video processor device 120 are assigned to these buttons. When the endoscope buttons 118a to 118c are operated, signals are transmitted to the endoscope CPU 115, and, if the functions assigned to the operated endoscope buttons 118a to 118c are functions of the endoscope 110, the endoscope CPU 115 executes processing that corresponds to those functions. Also, if the assigned function is a function performed by the video processor device 120, the endoscope CPU 115 transmits, to the video processor device 120, a signal for requesting execution of that function. The endoscope CPU 115 can also receive data from the video processor device 120 and perform signal processing and various types of operation adjustment based on the received data.

A capture operation is assigned to one of the endoscope buttons 118a to 118c. Specifically, when the endoscope button having the capture operation assigned thereto is operated, a still image is acquired by the endoscope 110 that had been acquiring a moving image for display on the monitor 150, the still image passes through the video processor device 120 and is sent to the filing device 140, and is then recorded in the memory of the filing device 140 as will be described later. Note that in capture processing, a configuration can be adopted in which a moving image having a predetermined duration is recorded in the filing device 140 instead of a still image.

The video processor device 120 includes a processor CPU 121, an internal storage unit 122, a processor memory 123, a light source 124, a signal processing unit 125, a processor timing controller 127, and the like.

The processor CPU 121 performs overall control of operation of the video processor device 120, and is also connected to the endoscope CPU 115, a filing CPU 144 of the filing device 140, and the like via connectors, and performs data communication with these CPUs. The processor memory 123 stores the device name, the production number, and the like of the video processor device 120. The signal processing unit 125 receives image data output from the analog signal processing circuit 112 of the endoscope 110, performs predetermined image processing including white balance adjustment processing, and outputs the processed image to the monitor 150. Note that the operation timing of units in the video processor device 120 and synchronization with the endoscope 110 are controlled based on signals from the processor timing controller 127.

The light source 124 is a halogen lamp, a xenon lamp, an LED lamp, or the like, and light therefrom passes through a condensing lens 128 and a diaphragm 129 and enters the light guide 117 mounted to the video processor device 120. The diaphragm 129 is constituted by a rotary shutter or the like, and adjusts the light quantity and emission timing of illumination light. The opening/closing and drive timing of the diaphragm 129 is controlled by a motor 130 that is connected to the processor CPU 121.

Also, a front panel 126 serving as an input means is connected to the processor CPU 121, and the front panel 126 is provided with multiple operation buttons and a display unit such as an LCD that displays setting menus and various types of information that the user is to be made aware of. By operating the operation buttons, the user can operate the endoscope system 100 and input necessary information, such as information regarding the observation target, to the video processor device 120.

The filing device 140 includes a device main body 141, a filing monitor 142, and a keyboard and mouse 143 that are filing input units, and is connected to the video processor device 120. The device main body 141 is provided with a filing CPU 144 and a filing storage unit 145, and the filing CPU 144 is connected to the processor CPU 121, the filing storage unit 145, the filing monitor 142, and an input unit 143 such as a keyboard/mouse. The filing storage unit 145 is a non-volatile memory, and files and stores captured images and various types of data regarding the endoscopic observation. The various types of data referred to here include white balance data corresponding to types of examination, and a database including the same. This white balance data (light source correspondence information) is stored in correspondence with multiple types of light sources such as the light source provided in the video processor device and the light source unit of a stroboscope device. The filing monitor 142 displays menus and lists of stored data, and the user inputs various types of data and performs setting by operating the input unit 143. Prior to use of the endoscope, the user inputs the type of examination and various types of data regarding the patient and consultation to the filing device 140.

The video processor device 120 is used along with a bronchosocope, a laryngoscope, a capsule endoscope, a colonoscope, an upper endoscope, a nasal endoscope, a duodenoscope, and the like. The following types of examination can be set in the endoscope system 100 (200) in correspondence with the aforementioned endoscopes. Specifically, a bronchoscope is used in bronchnoscopy (abbreviated as BRO hereinafter) for observation of the inside of bronchi, and a laryngoscope is used in stroboscopic observation. A capsule endoscope is used in capsule endoscopy, and a colonoscope is used in colonoscopy for observation of the inside of a colon. An upper endoscope is used in upper endoscopy for observation of the interior of an upper gastrointestinal tract (esophagus, stomach, etc.); a nasal endoscope is used in ear, nose, and throat endoscopy for observation of the ears, nose, and throat; and a duodenoscope is used in endoscopic retrograde cholangio-pancreatography (ERCP).

In these examination methods, the signal processing unit 125 performs image processing such as pixel enhancement that corresponds to the examination method, in order to allow the doctor to more accurately ascertain the affected part. Also, the endoscopes can also be used in examination methods in which other endoscopes are used. In this case, the signal processing unit 125 performs image processing such as pixel enhancement that corresponds to the observation target and examination objective. This image processing includes gain adjustment processing, white balance adjustment processing, edge enhancement processing, and pixel enhancement processing, for example. Gain adjustment processing is processing for adjusting the gain of image data and adjusting the signal level of image data to a level suited to observation. White balance adjustment processing is processing for adjusting the white balance of image data to improve the color tone. Edge enhancement processing is processing for enhancing edges in a subject image, such as the edges of an affected part, in order to clarify the affected part region and thus facilitate observation and discovery of the affected part. Pixel enhancement processing is processing for enhancing only reflected light of a specific wavelength, thus making it possible to facilitate viewing of an affected part that reflects light of that specific wavelength.

In the endoscope system 200 shown in FIG. 2, instead of the endoscope 110, an endoscope 210 is mounted to the video processor device 120. Also, a light source device 220 that is different from the video processor device 120 is used as the light source. Note that in FIG. 2, the configurations of the video processor device 120, the filing device 140, and the monitor 150 are similar to those in FIG. 1.

In the endoscope system 200 in FIG. 2, the endoscope 210 is a laryngoscope for example, and the light source device 220 is a stroboscope device (stroboscopic light source device) for example. A light guide 217 of the endoscope 210 is mounted to the light source device 220 and connected to a light source unit 221 in the light source device 220. The light source unit 221 is controlled by a stroboscope CPU 222, and supplies illumination light to the light guide 217 in accordance with a voice frequency input from a microphone 223, for example. Also, the stroboscope CPU 222 is connected to the video processor device 120 and a stroboscope storage unit 224, and exchanges data with the same. The stroboscope storage unit 224 is a non-volatile memory that stores the model name, serial number, and the like.

Note that the functions of an imaging element 211, an analog signal processing circuit 212, a drive circuit 213, a timing controller 214, an endoscope CPU 215, a memory 216, and endoscope buttons 218a to 218c in the endoscope 210 are similar to those of the imaging element 111, the analog signal processing circuit 112, the drive circuit 113, the timing controller 114, the endoscope CPU 115, the memory 116, and the endoscope buttons 118a to 118c of the endoscope 110.

Figure 3:
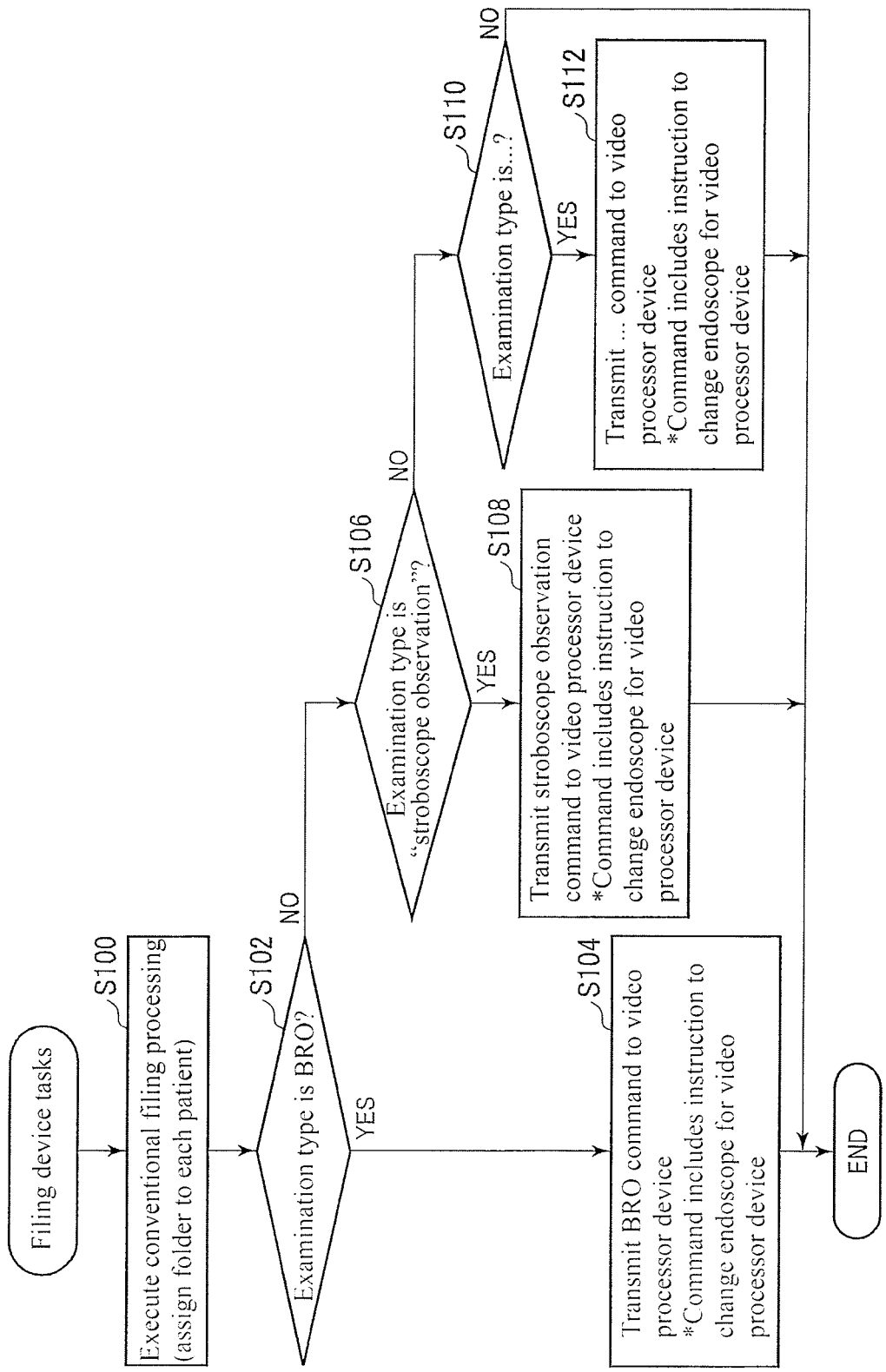
FIG. 3 is a flowchart of tasks executed by a filing device at the time of filing device startup.

FIG. 3 is a flowchart of tasks executed in the filing device 140 when an examination is to start (at the time of filing device 140 startup).

When the filing device 140 is turned on, and tasks are started, one of folders assigned to each patient is selected, or a new folder is created for a new patient, for example (step S100). Thereafter, it is determined whether or not the set type of examination is bronchoscopy (BRO) for example (step S102). If the type of examination is bronchoscopy (BRO), a command for bronchnoscopy (BRO) is transmitted to the video processor device 120 (step S104), and then this processing ends.

If the set type of examination is not bronchnoscopy (BRO) (step S102), it is determined whether or not the type of examination is stroboscopic observation (step S106). If it is determined that the type of examination is stroboscopic observation, a command for stroboscopic observation is transmitted to the video processor device 120 (step S108), and then this processing ends. If it is determined that the type of examination is not stroboscopic observation (step S106), it is similarly then successively determined whether or not the type of examination is a type of examination that can be set in the filing device 140 (represented by step S110). When the type of examination is identified, a command corresponding to that type of examination is transmitted to the video processor device 120 (represented by step S112), and then this processing ends.

Note that after this processing ends, the execution of later-described data communication processing and image capturing standby processing is repeatedly executed by the filing device 140 through interrupt processing, for example. Also, if the type of examination has not been set, the user is alerted of that fact, the procedure returns to step S100, and setting of the type of examination is prompted. Note that the command transmitted to the video processor device 120 (S104, S108, S112) includes an instruction to change the endoscope connected to the video processor device 120, as will be described later.

Figure 4:
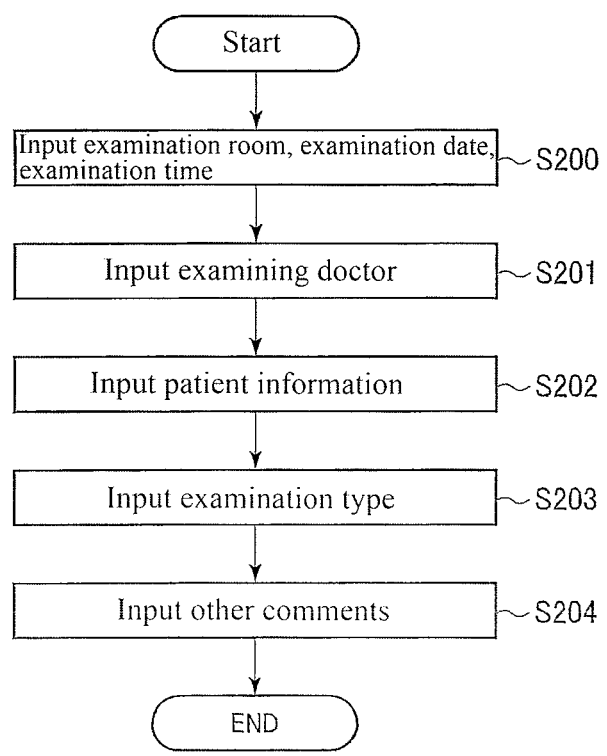
FIG. 4 is a flowchart of data input (during schedule creation) in step S100 in FIG. 3.

FIG. 4 is a flowchart of data input (during schedule creation) performed in step S100.

When schedule creation is started in step S100 in FIG. 3, the user first inputs data such as the examination room, the examination date, and the examination time (step S200), and then inputs the name of the examining doctor (step S201) and inputs patient information (patient's name, age, gender, etc.) (step S202). The user also sets (selects) the type of examination that is to be performed (step S203). Lastly, the user inputs other comments (step S204), and then the schedule creation of step S100 ends.

Figure 5:
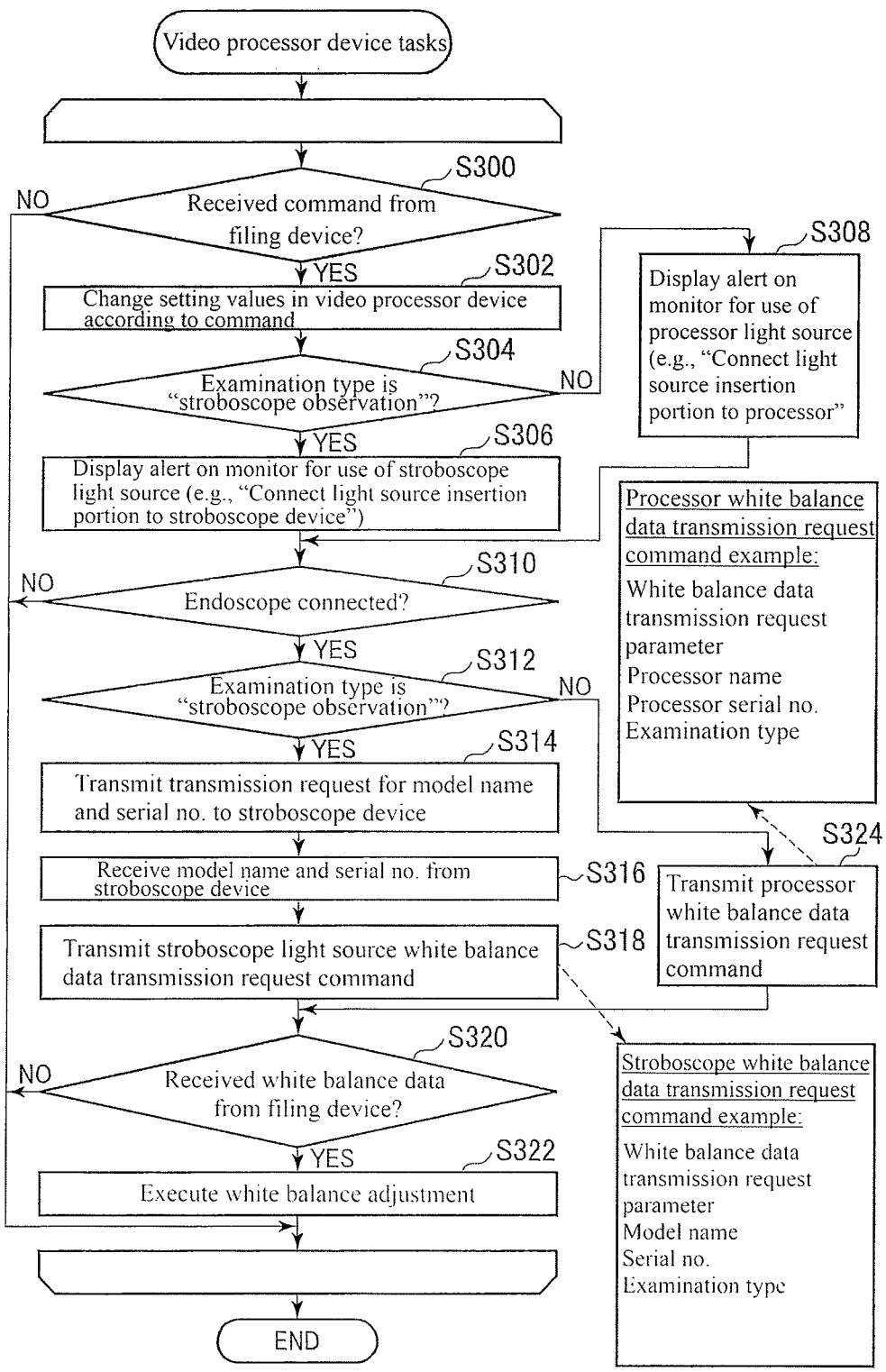
FIG. 5 is a flowchart showing a flow of tasks that are executed in a video processor device in order to perform data communication with the filing device.

FIG. 5 is a flowchart showing a flow of tasks executed in the video processor device 120 in order to perform data communication with the filing device 140. Note that this processing is periodically executed as interrupt processing, for example, in the processor CPU 121.

In this processing, first, it is determined whether or not a command was received from the filing device 140 (step S300). If a command has not been received, this processing ends, and other processing necessary to the video processor device 120 is performed. If a command is received from the filing device 140, setting values of the video processor device 120 are changed according to the received command (step S302), and it is determined whether or not the type of examination is "stroboscopic observation" (step S304).

If the type of examination is "stroboscopic observation", an alert message (included in the command from the filing device 140) such as "Connect light source insertion portion to stroboscope device" is displayed on the monitor 150 and the display of the front panel 126, thus prompting the user to use a stroboscope light source (step S306). If the type of examination is not "stroboscopic observation", an alert message (included in the command from the filing device 140) such as "Connect light source insertion portion to processor" is displayed on the monitor 150 and the display of the front panel 126, thus prompting the user to use the light source of the video processor device (step S308).

When the processing of step S306 or step S308 ends, it is determined whether or not an endoscope is connected (step S310). If an endoscope is not connected, this processing ends, and an alert instructing the connection of an endoscope is displayed, for example. Next, it is again determined whether or not the type of examination is "stroboscopic observation" (step S312), and if the type of examination is "stroboscopic observation", a transmission request that requests the model name and the serial number is output to the stroboscope CPU 222 of the stroboscope device (light source device) 220 that is connected (step S314), and this data (model name and serial number) is received from the stroboscope device (light source device) 220 (step S316).

Based on the model name and the serial number received from the stroboscope device (light source device) 220, the processor CPU 121 transmits, to the filing device 140, a request command for transmission of stroboscope light source white balance data (white balance parameters) that corresponds to the model name, serial number, and type of examination (step S318), and then determines whether or not white balance data was received from the filing device 140 (step S320). If white balance data has not been received, this processing is ended. On the other hand, if white balance data is received from the filing device 140 (step S320), RGB gain adjustment for white balance (white balance adjustment) is performed in the signal processing unit 125 based on the received data (step S322), and then this processing ends.

On the other hand, if it is determined in step S312 that the type of examination is not "stroboscopic observation", the model name and the serial number of the video processor device 120 and the type of examination are transmitted to the filing device 140, and a request command that requests white balance data that corresponds to the type of examination and the processor light source 124 is transmitted to the filing device 140 (step S324). Thereafter, it is determined whether or not white balance data was received from the filing device 140, the reception of data is waited for (step S320), and then when white balance data is received from the filing device 140, RGB gain adjustment for white balance (white balance adjustment) is performed in the signal processing unit 125 based on the received data (step S322), and then this processing is ended.

Figure 6:
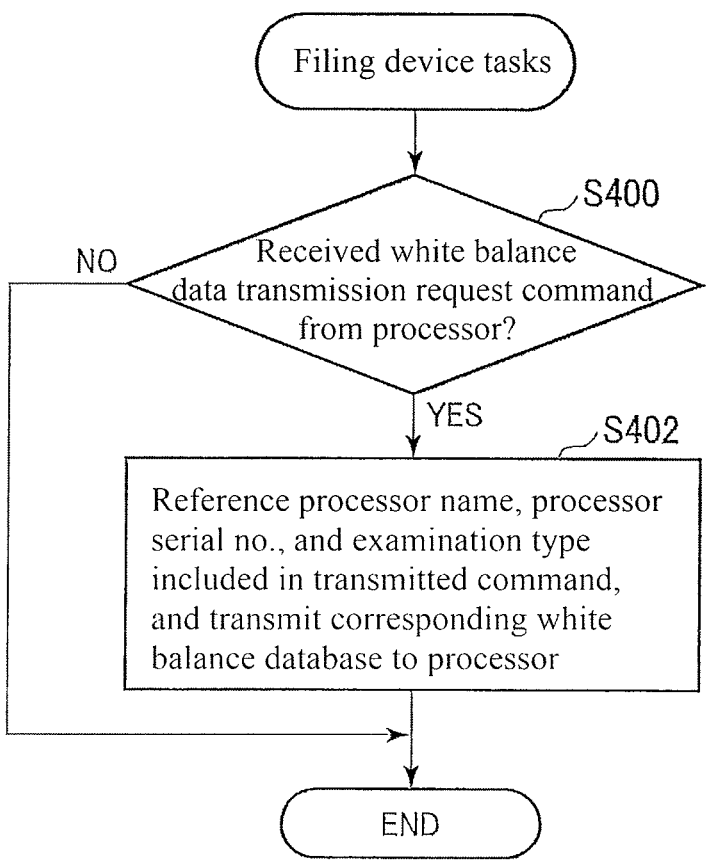
FIG. 6 is a flowchart showing a flow of tasks that are executed in the filing device in order to perform data communication with the video processor device.

FIG. 6 is a flowchart showing a flow of tasks executed in the filing device 140 in order to perform data communication with the video processor device 120, in accordance with tasks in the video processor device 120 in FIG. 5. Note that this processing is repeatedly executed as interrupt processing, for example, in the processor CPU 121.

In the filing CPU 144, it is determined whether or not a white balance data transmission request command was received from the video processor device 120 (step S400), and if it has been received, the model name (processor name) and the serial number of the processor and the type of examination, which are included in the transmitted command are referenced, corresponding white balance data is read out from the database in the filing storage unit 145 and transmitted to the video processor device 120 (step S402), and then this processing ends. Note that if a white balance transmission request command has not been received from the video processor device 120, this processing ends immediately.

Figure 7:
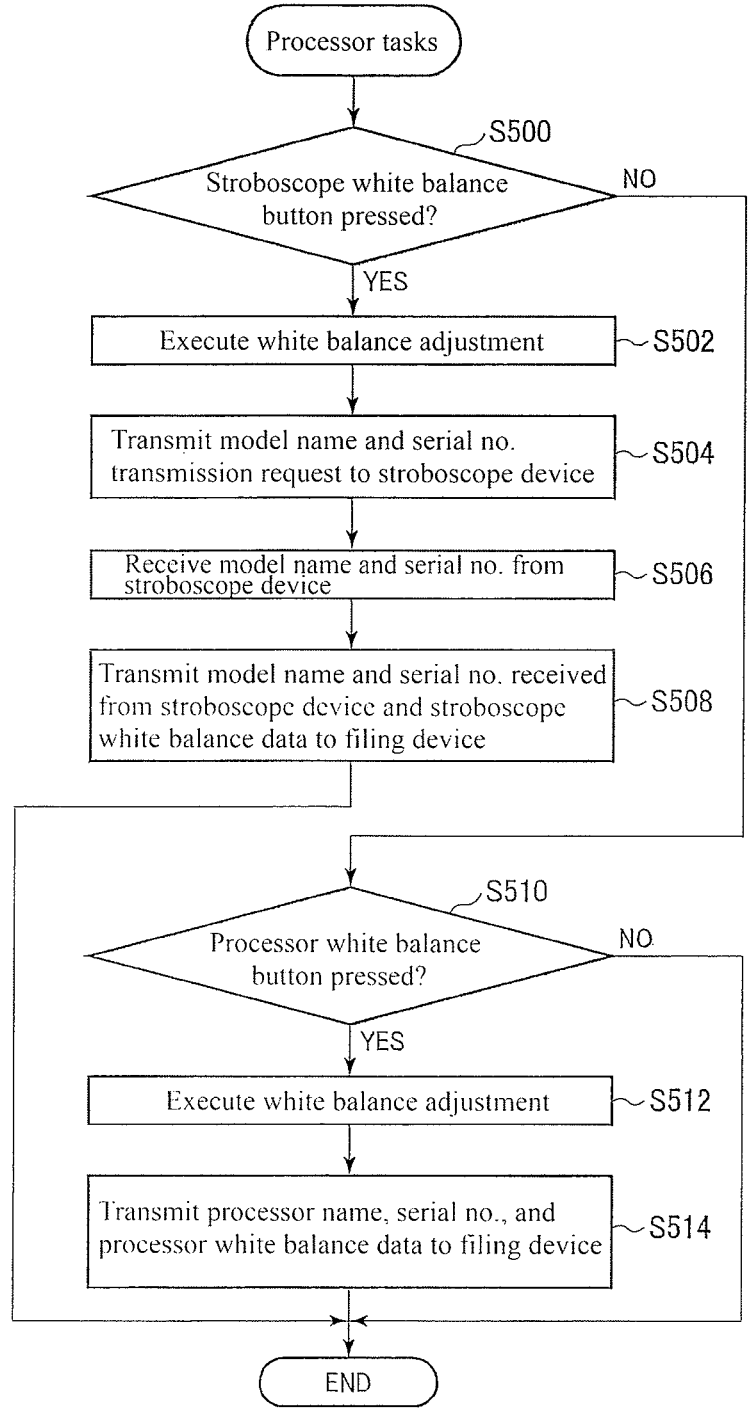
FIG. 7 is a flowchart of white balance adjustment operation tasks that are executed in the video processor device.

FIG. 7 is a flowchart of white balance adjustment operation tasks executed in the video processor device 120. This processing is performed while the user uses a jig that includes a white board, for example, and is repeatedly executed as interrupt processing in the processor CPU 121.

In this processing, it is determined whether or not a stroboscope light source white balance button, for example, provided on the front panel 126 was operated (step S500), and if it is determined that the stroboscope light source white balance button was operated, the white balance adjustment operation flow is executed (step S502). In other words, as conventionally known, the leading end of the endoscope is inserted into a jig by the user, an image of a white plate serving as a reference is captured, and the RGB gain ratio is adjusted to obtain a predetermined balance (white) in the image in the video processor device 120.

Thereafter, a request for transmission of the model name and the serial number is sent to the stroboscope device 220 (step S504), and the model name and the serial number are received from the stroboscope device 220 (step S506). The received model name and serial number of the stroboscope device 220 are transmitted, along with the RGB gain ratio (white balance data) obtained in step S502, to the filing device 140 (step S508), and then this processing ends.

On the other hand, if it is determined in step S500 that the stroboscope light source white balance button has not been operated, it is then determined whether or not a processor light source white balance button was operated (step S510). If it is determined that the processor light source white balance button was operated, similarly to step S502, the white balance adjustment operation flow is executed (step S512). The model name and the serial number of the processor device are transmitted, along with the white balance data obtained in step S512, to the filing device 140 (step S514), and then this processing ends. Note that if it is determined in step S510 that the video processor device white balance button has not been operated, that is to say, if neither of the stroboscope light source or processor light source white balance buttons has been operated, this processing ends immediately.

Figure 8:
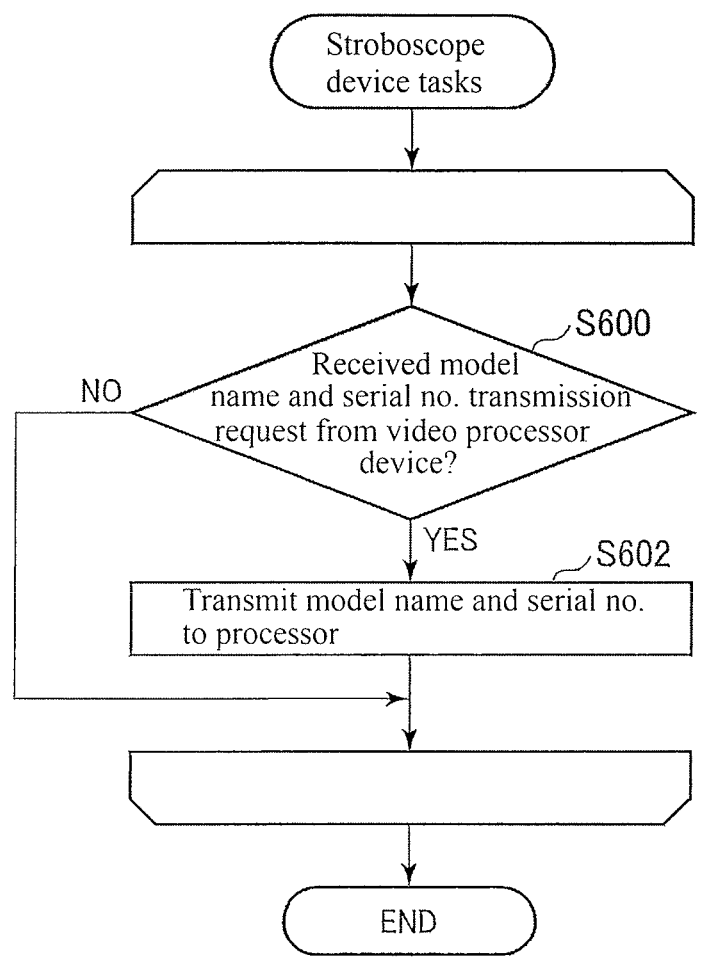
FIG. 8 is a flowchart of tasks that are executed in a stroboscope device in accordance with tasks in steps S504 and S506 in FIG. 7.

FIG. 8 is a flowchart of tasks executed in the stroboscope device 220, and this flowchart includes processing that corresponds to the tasks of steps S504 and 506 in FIG. 7. Note that the flow shown in FIG. 8 is repeatedly executed as interrupt processing, for example, in the stroboscope CPU 222. This flow is constituted by processing for determining whether or not a model name and serial number transmission request was received from the video processor device 120 (step S600), and processing for, if such a transmission request was received, reading out the model name and the serial number from the stroboscope storage unit 224 and transmitting them to the video processor device 120 (step S602).

Figure 9:
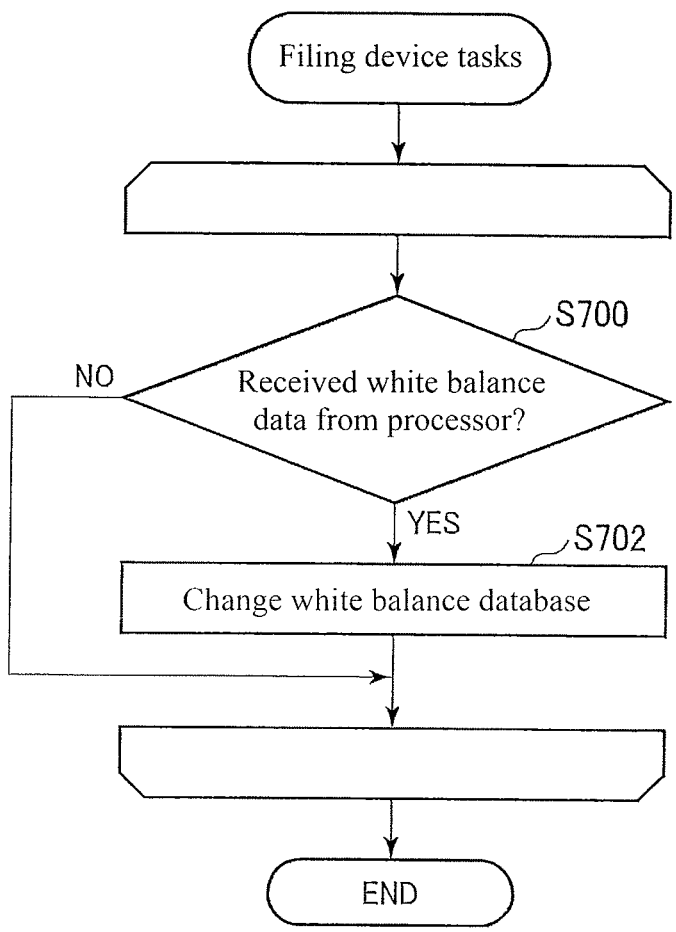
FIG. 9 is a flowchart of tasks that are executed in the filing device in accordance with the task in step S508 in FIG. 7.

Next, FIG. 9 is a flowchart of tasks executed in the filing device 140, which include processing corresponding to the task of step S508 in FIG. 7, and this flow is repeatedly executed as interrupt processing, for example, in the filing CPU 144. In the flow in FIG. 9, it is determined whether or not a model name, a serial number, and white balance data corresponding thereto was received from the video processor device 120 (step S700), and if such data was received, the database in the filing storage unit 145 is accessed, and white balance data corresponding to the model name and the serial number is updated or newly created (step S702).

As described above, according to the endoscope systems of the present embodiment, in an endoscope system in which various combinations of multiple types of light sources (e.g., a processor light source or a stroboscope light source), video processors, and endoscopes are used, information regarding the light source such as white balance data can be centrally managed by a filing device that is used in common by multiple video processor devices, thereby eliminating the need for the same information to be stored in each video processor device, and improving operation efficiency. Also, this system can be easily applied to conventional video processor devices as well, and replacement with this system is easy.

Note that although information corresponding to light sources is stored in the filing device in the present embodiment, such information is not limited to being stored in a filing device, and may be stored in any external device that can be used in common with multiple video processor devices, and it is possible to use an externally connected device that is dedicated to the central management of information corresponding to light sources. Also, the present embodiment is also applicable to the case where a video processor device includes multiple light sources.

DESCRIPTION OF REFERENCE SIGNS

100 Electronic endoscope system
110, 210 Endoscope
117, 217 Light guide
120 Video processor device
121 Processor CPU
123 Memory
124 Processor light source
125 Signal processing unit
126 Front panel
140 Filing device
144 Filing CPU
145 Filing storage unit
150 Monitor
220 Stroboscope device
221 Light source unit
222 Stroboscope CPU
223 Microphone
224 Stroboscope storage unit

The invention claimed is:

1. An endoscope system comprising:
a video processor device that performs signal processing on an image; and
a filing device that is removably connected to the video processor device, the filing device including:
a filing CPU operatively connected to a CPU of the video processor device;
a filing memory operatively connected to the filing CPU and stores the image and data regarding light source correspondence information that corresponds to a plurality of light sources;
a filing monitor that displays menus and lists of data stored in the filing memory; and
an input unit that receives user input regarding endoscopic examination,
wherein the CPU of the video processor device acquires the light source correspondence information from the filing memory via the filing CPU and performs signal processing that corresponds to the light source correspondence information.

2. The endoscope system according to claim 1, wherein the user input includes data for setting a type of examination, and the video processor device acquires, from the filing memory via the filing CPU, light source correspondence information that corresponds to a type of examination that was set.

3. The endoscope system according to claim 2, wherein the video processor device displays a message that corresponds to a type of examination that was set.

4. The endoscope system according to claim 1, wherein the light source correspondence information includes a white balance parameter, and the signal processing includes white balance adjustment processing.

5. The endoscope system according to claim 1, further comprising a light source device that is independent of the video processor device, wherein the filing device can record light source correspondence information that corresponds to the light source device, and the video processor device can perform signal processing that corresponds to a light source of the light source device.

6. The endoscope system according to claim 1, wherein the video processor device includes one or more light sources, and the signal processing is performed based on the light source correspondence information that corresponds to a light source being used.

* * * * *